US005635167A

United States Patent [19]

Said et al.

[11] Patent Number: 5,635,167

[45] Date of Patent: Jun. 3, 1997

[54] REMOVAL OF MINERALS FROM HUMAN HAIR AND ANIMAL KERATIN FIBERS

[75] Inventors: Hayel Said; Hian Said, both of Simi Valley, Calif.

[73] Assignee: L'Avante Garde, Inc., Simi Valley, Calif.

[21] Appl. No.: 365,594

[22] Filed: Dec. 28, 1994

[51] Int. Cl.$^6$ .................................................... A61K 7/06

[52] U.S. Cl. ................. 424/701; 424/70.11; 424/DIG. 6; 132/202

[58] Field of Search ......................... 424/45, 70.1, 70.11, 424/DIG. 6; 132/202; 252/DIG. 11

[56] References Cited

U.S. PATENT DOCUMENTS

| | | | |
|---|---|---|---|
| 3,578,387 | 5/1971 | Zviak et al. | 8/10.1 |
| 4,581,229 | 4/1986 | Petrow | 424/70.11 |
| 4,690,818 | 9/1987 | Puchalski, Jr. et al. | 424/70.11 |

FOREIGN PATENT DOCUMENTS

| | | |
|---|---|---|
| 9311737 | 6/1993 | WIPO . |

OTHER PUBLICATIONS

Weber, Nelson, Vaquera, Pearson, titled "Trace Elements in the Hair of Healthy and Malnourished Children", J. Trop. Ped., 36 (1990) 230–234.

Roomans and Forslind, titled "Copper In Green Hair: A Quantitative Investigation by Electron Probe X-Ray Microanalysis", Ultrastructural Pathology, 1 (1980) 301–307.

Edman and Marti, titled, "Properties of Peroxide-Bleached Hair", J. Soc. Cos. Chem., 12 (1961) 133–145.

Hilderbrand & White, titled "Trace-Element Analysis in Hair: An Evaluation", Clin. Chem. 20(2) (1974) 148–151.

Holmes & Goldsmith, titled "The Man with Green Hair", N.E.J. Med., 291 (1974) 1037.

Nordlund, Hartley and Fister, titled "On the Cause of Green Hair", Arch. Dermatol., 113 (1977) 1700.

Assarian and Oberleas, titled "Effect of Washing Procedures on Trace Element Content of Hair", Clin. Chem. 23(9) (1977).

McKenzie, titled "Alteration of the Zinc and Copper Concentration of Hair", Am. J. Clin. Nutr., 31 (1978) 470–76.

Bhat, Lukenbach, Kennedy and Parreira, titled "The Green Hair Problem: A Preliminary Investigation", J. Soc. Cosmet. Chem. 30 (1979) 1–8.

Buckley and Dreosti, titled "Radioisotopic Studies Concerning the Efficacy of Standard Washing Procedures for the Cleansing of Hair before Zinc Analysis", Am. J. Clin. Nutr., 40 (1984) 840–46.

Wilhelm, Ohnesorge, Lombeck and Hafner, titled "Uptake of Aluminum, Cadmium, Copper, Lead, and Zinc by Human Scalp Hair and Elution of the Absorbed Metals", J. Anal. Tox., 13 (1989) 17–21.

Budavari, S., et al. (1989). The Merck Index. Merck & Co., Inc., p. 550.

*Primary Examiner*—Raj Bawa
*Attorney, Agent, or Firm*—Oldham & Oldham Co., L.P.A.

[57] ABSTRACT

This invention describes a process for the removal of exogenous minerals which have become attached to human hair or keratin fiber which include the steps of contacting at least one chelating agent to the human hair or keratin fiber, the chelating agent selected from the group consisting of amino acid-type, polyphosphate-type and phosphonate-type agents, maintaining contact with the chelating agent and the human hair or keratin fiber for a period of time sufficient to permit the chelating agent to complex with the exogenous minerals, thereby removing at least a portion of the attached minerals, and rinsing the chelating agent. The process is enhanced with the pH is adjusted to a range of between 4 to 9, preferably 5 to 8. The chelating agent is added at a concentration of 4% by weight to 25% by weight, preferably 5 to 20% by weight. In a preferred case, the chelating agent is selected from the group consisting of a salt of ethylenediaminetetraacetic acid, a salt of hydroxyethylethylenediaminetriacetic acid, a salt of diethylenetriaminepentaacetic acid, a salt of nitrilotriacetic acid and a salt of tripolyphosphate, preferably the sodium salt. The chelating agents used are preferably blends of chelating agents thereby achieve a synergistic effect.

20 Claims, No Drawings

REMOVAL OF MINERALS FROM HUMAN HAIR AND ANIMAL KERATIN FIBERS

TECHNICAL FIELD

This invention relates to a hair treatment capable of cleansing human hair and other animal keratin fibers of mineral deposits in the form of multivalent metals such as copper, iron, lead, zinc, aluminum, cadmium, and those known as water hardness minerals such as calcium, magnesium and others.

BACKGROUND OF THE INVENTION

Deposition of minerals in hair is an unavoidable phenomenon. Well water, used by many communities around the country and around the world, is enriched with a wide array of minerals. Copper and iron ions can also leach from pipes into water, especially where water supplies are chlorinated periodically. Swimmers encounter a constant source of copper in the form of certain algicides added frequently to swimming pools. Many of the swimmers develop a greenish tint as copper accumulates in their hair. This greenish tint is independent of hair type or color. Dark and brown hair adsorb as much copper as light blonde hair although the greenish color obviously is not readily visible.

Many cosmetic hair products contain, by design, certain amounts of minerals, such as magnesium, iron or copper to perform specific functions. Products which fall into this category include hair conditioners containing magnesium sulfate and hair colorants containing lead acetate, henna, other plant extracts, or metallic pretreatments.

Hair is a strong adsorbent of these metals. Binding is so strong that once these multivalent cations are captured by the anionic sites on the fiber, they are hard to elute off these sites. As a result, there is a gradual metallic build-up which only intensifies with time. The extent to which minerals in general bind to hair depends on several factors such as condition and porosity, length of the fiber, and levels as well as duration of exposure.

This metal build-up can lead to a range of undesirable, and sometimes adverse, effects. Metals like copper, lead and iron, can interfere with chemical treatments such as hair coloring and permanent waving. Iron- and/or copper-contaminated hair may experience uneven and unpredicted color deposit because of variations in hair porosity and mineral build-up. Such variations in mineral build-up lead to differences in the rate of catalysis and formation of dye molecules along the length of the hair shaft, causing the uneven color deposit. Iron can also interfere with permanent waving, by reacting with reducing agents such as thioglycolic acid and its derivatives, to produce an undesirable purple color. Both iron and copper can catalyze the decomposition of the peroxide in the neutralizing solution of the rebonding step, hence reducing its capacity to fully reoxidize the thiol groups. This can lead to a weakened perm and a fragile hair.

Metal build-up can also result in serious breakaway exothermic reactions which may precipitate severe injury to the scalp and facial areas. An example of such a nightmare experienced by the majority of salon operators, is during bleaching or highlighting of hair significantly contaminated with heavy metals. The temperature under these circumstances may rise to the boiling point in as little as five minutes.

Normal levels of minerals in uncontaminated hair have been measured by several investigators and the following concentration ranges have been reported: copper, 17–38 parts per million (ppm); calcium, 140–2450 ppm; magnesium, 20–450 ppm; iron, 6–300 ppm; and lead, 5–7 ppm (Weber et. al., J. Tropical Pediatrics (1990) 36:230–34). When build-up levels significantly exceed the normal ranges, due to exogenous accumulation, discoloration of the hair becomes visible. Iron casts a typical rusty look to the hair, lead gives it a black tone, copper deposits a greenish tint, while calcium and magnesium deposits are colorless. In the reported cases of green hair, the depth of the greenish tint is proportional to the amount of copper adsorbed onto the hair. A hint of green can be noticed on light blonde hair at copper levels as low as 300 ppm. Copper content of hair from people with green hair fluctuates through a wide range, and values of 1500 to 17500 ppm have been reported by different investigators (Roomans and Forslind, Ultrastruc. Pathol., (1980) 1:301–7). A value of about 5000 ppm has been documented quite frequently. In the laboratory, levels as high as 34,000 ppm have been recorded when extensively bleached hair was used (Edman and Marti, J. Soc. Cosmet. Chem. (1961) 12:133–45).

The problem of mineral adsorption by the hair has been seriously addressed during the last three decades, and many efforts have been directed towards finding a remedy, but none has been very successful. As far back as half a century ago, hair dressers recommended hot oil treatment for removing the green tint from hair. In addition to being messy, the remedy is for the most part, ineffective. Hilderbrand and White (Clin. Chem. (1974) 20:148–51) tried several washing procedures which included the chelating agent ethylenediaminetetra-acetic acid disodium salt (EDTA-$Na_2$). Their conclusion was that no significant effect was observed with removal of copper, and only partial success was attained with removal of calcium, magnesium and zinc. Similarly, Holmes and Goldsmith (New Engl. J. Med. (1974) 291:1037) were not able to remove the green tint from hair with either water, acetone, ethanol, or hexane extraction. Following a parallel path, Nordlund et. al. (Arch. Dermatol. (1977) 113:1700) found that elements adsorbed to the hair resist elution by washing, boiling, organic solvents and EDTA. They concluded that standard wash procedures do not remove exogenously adsorbed metals. Using a more drastic procedure, Assarian and Oberleas (Clin. Chem. (1977) 23:1771–2) found that only 45% of copper could be removed by a wash system containing a combination of harsh organic solvents such as acetone and ether, and detergents. Under conditions of high contamination of zinc and copper, McKenzie (Am. J. Clin. Nutr. (1978) 31:470–80) reported that a cleansing solution containing EDTA-$Na_2$ and a detergent could not elute all the copper.

In the late seventies, Ramachandra et. al. (J. Soc. Cosmet. Chem. (1979) 30:1–8), after experimenting with several cleansing treatments, showed that the adsorbed copper and the resultant green color cannot be washed off by normal shampooing or treatment with a detergent. In studies employing radioisotopes, Buckley et. al. (Am. J. Clin. Nutr. (1984) 40:840–46) noted that in all cases studied, no evidence was found that any washing procedure effectively removed all exogenous metal. More recently, Wilhelm et. al. (J. Anal. Toxicol. (1989) 13:17–21) tested the efficacy of EDTA and detergent solutions in removing adsorbed metals. Their conclusion also was that the removal of adsorbed elements after treatment with various metal-enriched aqueous solutions is not very effective.

The patent literature reveals very few references to the problem of metal contaminants in hair or other keratin fibers. U.S. Pat. No. 4,581,229, teaches of a composition based on lanthanum salts for removing heavy metals from hair. The reference is deficient for two reasons: (1) in the case of iron contaminated-hair, the level of contamination in the tested samples was too low (about 160 ppm) to give any statistical significance; and (2) in the case of copper, no quantitative data is presented other than the qualitative statement indicating a reduction of the greenish color. The patent, however, warns against the use of chelating and complexing agents in conjunction with lanthanum salts because of undesirable effects. On the other hand, U.S. Pat. No. 4,690,818 teaches of a cleansing formulation intended for conditioning and moisturizing of hair and/or skin. The formulation utilizes low levels (0.001–0.5%) of EDTA salts to remove metals from water and soften it during washing of hair or skin. In this instance, EDTA is used to sequester metal ions from the washing water and not the hair, and no claims of metal removal from hair are made. As will be shown below (Table 4), EDTA levels twenty times as high as the upper limit of what is specified in this patent, are ineffective for total removal of hair metal contaminants.

More recently, International Patent Application, No. WO 93/11737, filed Jun. 24, 1993 disclosed a composition for the removal of minerals, which includes the combination of acidifying agent, reducing agent, chelating agent, and gelling agent. The reasoning behind this composition is that, since chelation with EDTA had only marginal efficiency, the inclusion of an acidifying agent and a reducing agent was required to weaken the bonds between the minerals and the hair proteins.

In spite of the documented scientific and patent literature attesting to the absence of an effective hair cleansing treatment for metal contaminants, there are numerous commercial products on the market which claim the ability to demineralize contaminated hair. These claims are usually made, based on the mere inclusion in these products of a chelating agent. As pointed out in the literature review earlier, and as will be shown below, there is very little validity for these claims.

A metal-cleansing treatment for hair, wool, and other keratin material, therefore, is desperately needed. This cleansing treatment should be safe, effective against a wide range of divalent and trivalent metals, and mild enough to lift only metal and soil contaminants from the hair without modifying its color or affecting the integrity and structure of the fiber.

SUMMARY OF THE INVENTION

In accordance with the present invention, there is provided a process for removing exogenous minerals from hair and other keratin fibers.

It is an object of this invention to achieve the removal of exogenous hair minerals by blends of specialized chelating molecules selected from the amino acid-type, polyphosphate-type, or phosphonate-type chelating agents.

It is a further object of this invention to effect the removal of exogenous hair minerals using blends of chelating molecules described above in the pH range of 4 to 9, with a preferred range of 5 to 8.

It is a still further object of this invention to effect the removal of the exogenous hair minerals by the above process using the chelating molecules at a minimal concentration of 4% by weight of the product in which they are incorporated, and a maximum concentration of 25%, with a preferred range of 5–20%.

These and other objects of this invention will be evident when viewed in light of the experimental data, detailed description, and appended claims.

DETAILED DESCRIPTION OF THE INVENTION

The foundations underlying the present invention have been established based on extensive studies and thorough research into the interaction of chelating agents with hair fibers, and the conditions which enhance their efficacy in removing even the most stubborn minerals from hair.

In order to scientifically test the effectiveness of any hair composition on the removal of exogenous metals, the following procedure was adopted:

(1) Preparing metal-contaminated hair by subjecting bleached hair swatches to the following treatments: (1) for copper-contaminated hair, swatches were soaked, while mixing at 25° C., in 0.5% solution of cupric chloride ($CuCl_2 \cdot 2H_2O$) for ten minutes at a solution to hair ratio of 100:1 the bleached hair under these circumstances develops a distinct green tint, and may contain between 5000 and 10,000 ppm of adsorbed copper, depending on the condition of the hair; and (2) for iron-contaminated hair, bleached swatches were soaked in 0.5% ferric chloride ($FeCl_3 \cdot 6H_2O$) solution for four hours at a solution to hair ratio of 100:1—the hair develops a light reddish brown tint, and may contain approximately 3000 ppm of adsorbed iron;

(2) Rinsing and shampooing the contaminated hair with a regular shampoo. The metallic tint is not affected by this shampooing step;

(3) Treating the contaminated hair swatch with the composition to be tested at a weight ratio of 1:1, according to specified instructions;

(4) Wrapping the composition-treated hair in aluminum foil and placing it in an oven at a temperature of 55° C. for an indicated period of time, this temperature having been selected because it approximates the temperature of a salon hood dryer;

(5) Rinsing and shampooing the hair at the end of treatment; and (6) Analyzing the treated hair for the content of residual metal, by either inductively-coupled plasma (ICP) or atomic absorption (AA) spectroscopy, and comparing this metal content to that of contaminated, non-treated controls. The values reported represent the residual content of metals (expressed in parts per million, ppm) after each designated treatment.

When ICP was used, hair samples were digested according to EPA Method and analyzed by EPA Method 6010. When AA was used, the samples were ashed in accordance with ASTM Method D 3516 and analyzed by ASTM Method D 4085-81. Both methods yielded comparable results.

Based on the studies conducted, and the surprising results as illustrated by the examples below, the invention discloses several blends of specialized chelating molecules which act in a synergistic manner to remove the most stubborn mineral contaminants from hair, within a pH range of 4–9, and a concentration range of 4–25%.

The specialized chelating molecules belong to three classes. The first class, which yielded the best results, includes chelating molecules of the amino acid type represented by formula (I)

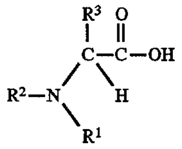

(I)

where $R^1$ is $CH_2$—Y;

Y is selected from the group consisting of $CO_2M$, $CH_2OH$, and H;

M is selected from the group consisting of H, Na, and K;

$R^2$ is represented by formula (II);

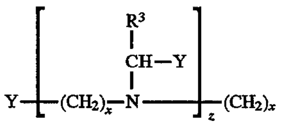

(II)

Y is as previously defined;

x is an integer subscript ranging from 0 to 4;

z is an integer subscript ranging from 0 to 3; and $R^3$ is selected from the group consisting of H and a phenyl moiety represented by formula (III)

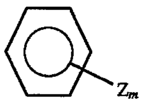

(III)

where Z is an hydroxyl group and m is a subscript ranging from 0 to 3.

In a preferred embodiment, representative examples of the amino acid type chelating agents would include (the common name with associated chemical abstracts registry number shown in parentheses): ethylenediaminetetraacetic acid (60-00-4); ethylenediaminetetraacetic acid, disodium salt (139-33-3); ethylenediaminetetraacetic acid, trisodium salt (150-38-9); ethylenediaminetetraacetic acid, tetrasodium salt (64-02-8); hydroxyethylethylenediaminetriacetic acid (150-39-0); hydroxyethylethylenediaminetriacetic acid, trisodium salt (139-89-9); nitrilotriacetic acid (139-13-9); nitrilotriacetic acid, trisodium salt (5064-31-3); ethanoldiglycine, disodium salt (135-37-5); ethylenebis (hydroxyphenylglycine) (1170-02-1); N-dihydroxyethylglycine (150-25-4); N-dihydroxyethylglycine, sodium salt (139-41-3); diethylenetriaminepentaacetic acid (67-43-6); and diethylenetriaminepentaacetic acid, pentasodium salt (140-01-2). In a most preferred embodiment, the amino-acid type chelating agents would be used as blend solutions.

The second class of specialized chelating molecules, which gave acceptable results, includes molecules of the polyphosphate type which contain more than one P atom and having P—O—P bonds. These polyphosphate chelating agents can be linear, and are generally represented as formula (IV)

$$[P_nO_{3n+1}]^{(n+2)-}M_{n+2}^{+} \qquad (IV)$$

where M is as defined previously. Examples would include $M_4P_2O_7$, a pyrophosphate or dipolyphosphate, and $M_5P_3O_{10}$, a tripolyphosphate. These polyphosphates can also be cyclic, and are generally salts of anions of general formula (V)

$$[P_nO_{3n}]^{n-}M_n^{+} \qquad (V)$$

where M is as defined previously. Examples would include $M_3P_3O_9$, a trimetaphosphate, and $M_4P_4O_{12}$, a tetrametaphosphate.

In a preferred example, representative examples would include, among others, the tripolyphosphates, tetrapyrophosphates, and hexametaphosphates, etc., namely: sodium tripolyphosphate (7758-29-4); potassium tripolyphosphate (13845-36-8); tetrasodium diphosphate (7722-88-5); hexametaphosphoric acid (18694-07-0); and sodium metaphosphate (10124-56-8).

The third class of chelating agents includes molecules of the phosphonate type, generally derived from phosphorous acid and are selected from the group consisting of formula (VI)

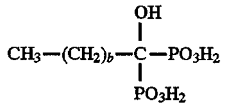

(VI)

and formula (VII)

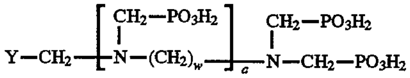

(VII)

where b is an integer subscript from 0 to 6;

a is an integer from 0 to 3;

w is an integer subscript from 2 to 8; and

Y is as previously defined.

In a preferred embodiment, phosphonate type chelating agents are selected from the group which would include: 1-hydroxyethane-1,1-diphosphonic acid (2809-21-4); amino (trimethylenephosphonic acid) (6429-29-8); 2-hydroxyethyliminobis(methylenephosphonic acid) (5995-42-6); diethylenetriaminepenta(methylenephosphonic acid) (22042-96-2); and bis(hexamethylene)triamine (pentamethylenephosphonic acid) (34690-00-1).

The present invention, in any form or composition, is applied to the hair and massaged thoroughly into the hair strands. A cap may be placed over the head, and heat from a dryer applied for five minutes if mineral contamination is moderate, or 15 minutes if contamination is heavy. Although heat is recommended for the successful removal of hair minerals, lightly contaminated hair may be processed at ambient temperature for 2 to 5 minutes.

Because of the numerous possible combinations that can be generated by the various specialized chelating molecules investigated by the present invention, only a few examples of possible compositions are provided in Table 5 for demonstrative purposes. These examples are not intended to limit the scope of the invention in any way. Aesthetic additives such as conditioners, fragrance, preservatives, thickeners, opacifying agents, pearlescing agents, lubricating agents, sunscreens, etc., have been omitted for simplicity because they do not generally affect the performance of these or similar compositions. The various combinations and ratios of the specified chelating agents may be employed depending on the problem mineral at hand. For example, if iron is the predominant hair contaminant, a formulation may be compounded with disodium ethanoldiglycine as the major component of the chelating blend. Whereas, for water hardness, the tetrasodium form of EDTA may be the dominant chelating agent. In all cases, however, blends of two or more chelating agents performed better than a single agent at equivalent concentrations and pH, as will be shown below in Table 2.

The best mode for carrying out the invention will now be described for the purposes of illustrating the best mode known to the applicant at the time. The examples are illustrative only and not meant to limit the invention, as measured by the scope and spirit of the claims.

EXAMPLES

Example #1

The efficacy of the composition of World Patent Appl. No. WO 93/11737 was tested according to the procedure adopted above. A mild baby shampoo was also included in the test as a control to account for heat-related effects and establish a base line.

Hair containing 7674 ppm of copper was treated with World Patent Appl. No. WO 93/11737 for either 15 minutes, or 45 minutes at 55° C. In comparison, Johnson's Baby shampoo, which is not a professional product, was applied for only 15 minutes at the same temperature.

Upon close analysis of the hair treated with the World Patent Appl. No. WO 93/11737, a very surprising observation was made. After treatment of the copper-contaminated hair with this composition, the greenish tint disappeared from hair giving the impression that copper has been removed. However, when this composition-treated hair was subjected to elemental analysis, the copper content of the hair was still very high, and only marginally better than the hair treated with the mild baby shampoo. When the composition-treated hair was rinsed with a weak solution of hydrogen peroxide, or left in the open for a few days, the greenish tint reappeared.

TABLE 1

| Sample Description | Residual copper (ppm) |
|---|---|
| Copper-contaminated hair (Cu-hair), control | 7674 |
| Cu-hair + Johnson's Baby shampoo(1) (15 min @ 55° C.) | 4215 |
| Cu-hair + WO 93/11737 composition (15 min @ 55° C.) | 4011 |
| Cu-hair + WO 93/11737 composition (45 min @ 55° C.) | 3368 |

(1)a product of Johnson & Johnson of Skillman, NJ.

It is concluded from the above test that the system of the composition of World Patent Appl. No. WO 93/11737 is masking the copper rather than removing it and, therefore, is ineffective for cleansing copper-contaminated hair. The composition's reducing system was effective, however, in removing iron which is not as stubborn a contaminant as copper.

Beside being ineffective in cleansing copper-contaminated hair, composition WO 93/11737, with its reliance on reducing agents, suffers from another drawback, namely, the lack of stability when exposed to air such as in a bottle of shampoo. Compositions of this type are usually packaged for a one-time use in a sealed packet which adds to their cost, or in a powder form which makes them tedious to mix and work with.

Example #2

A comparison of the efficacy of some chelating agents and blends thereof, as revealed by the present invention, is shown in Table 2, in relation to the removal of copper from Cu-contaminated hair. In comparing the sodium salts of EDTA, used in the great majority of prior art, it was verified that these salts are marginally effective in removing metals from contaminated hair, under conditions of use by prior art. However, other amino acid-type chelating agents such as hydroxyethylenediaminetriacetic acid salts (HEEDTA-$Na_3$), nitrilotriacetate (NTA-$Na_3$), and pentasodium diethylenetriamine-pentaacetate (DTPA-$Na_5$) are shown by the present invention to be more effective than EDTA salts. Copper-contaminated hair containing 5260 ppm Cu was treated with the indicated chelating agents, all adjusted to pH 7.0 before use, for 5 minutes at 55° C. Quite surprisingly, the present invention has discovered that blends of specific chelating agents, are even more potent than any individual agent. This discovery of a synergistic effect is clearly illustrated by the data in the Table where a blend consisting of 2% EDTA-$Na_4$, 2% HEEDTA-$Na_3$, and 1% ethanoldiglycine (EDG) proved to be more effective than any of its components.

TABLE 2

| Sample & Treatment | Residual copper (ppm) |
|---|---|
| Copper-contaminated hair (Cu-hair), control | 5260 |
| Cu-hair + 5% EDTA-$Na_2$ | 1565 |
| Cu-hair + 5% EDTA-$Na_4$ | 1665 |
| Cu-hair + 5% HEEDTA-$Na_5$ | 850 |
| Cu-hair + 5% NTA-$Na_3$ | 780 |
| Cu-hair + 5% EDG-$Na_2$ | 2460 |
| Cu-hair + 5% blend(1) | 500 |

(1)2% EDTA-$Na_4$, 2% HEEDTA-$Na_3$, and 1% EDG

Example #3

International Patent Application No. WO 93/11737 specifies an acidic pH of 2.5 for its reducing composition, while chelation literature in general, recommends high pH ranges for effective removal of divalent cations. The present invention has demonstrated that a low pH hampers the chelation and removal of copper and iron from contaminated hair. Unexpectedly, the present invention has also demonstrated that a high pH similarly retards the chelation of these metals from hair fibers. This pH effect on copper and iron removal from copper- or iron-contaminated hair is shown in Table 3. In these studies, hair swatches, separately contaminated with either copper or iron were treated with an invention blend adjusted to the specified pH, and placed for 5 minutes in an oven at 55° C. The invention blend consisted of 3.5% EDTA-$Na_4$, 5% HEEDTA-$Na_3$, 2% EDG, and 0.5% xanthan gum. Xanthan gum is a high molecular weight hetero polysaccharide gum obtained through fermentation processes and is typically used in various cosmetic products as a thickener to impart gel-like character to aqueous media. The values of copper and iron indicate the content of the metals remaining in the hair after treatments. These observations which are summarized in the following Table 3, show that pH ranges below 4 and above 9 decrease the efficiency of metal removal from hair. A pH-related efficiency peak for the removal of metal contaminants has been identified by the present invention to be around pH 7.5.

TABLE 3

| Treatment | Residual copper (ppm) | Residual iron (ppm) |
|---|---|---|
| Metal-contaminated hair, untreated (control) | 7674 | 3671 |
| Invention blend[(1)] (pH 3.0) | 2983 | 981 |
| Invention blend[(1)] (pH 4.0) | 2264 | 896 |
| Invention blend[(1)] (pH 7.5) | 725 | 250 |
| Invention blend[(1)] (pH 10.0) | 1918 | 536 |
| Invention blend[(1)] (pH 11.0) | 2044 | 814 |

[(1)]3.5% EDTA-$Na_4$, 5% HEEDTA-$Na_3$, 2% EDG, and .5% xanthan gum

Example #4

The present invention has uncovered an unexpected dose relationship between the blend of specialized chelating agents required, and the content of metal contaminants. This dose is approximately twenty parts of chelating agents for every part of mineral in the hair, a ratio which is about four times higher than published theoretical estimates for chelation of minerals in solution. This means that a hair containing 5000 ppm (0.5%) of copper, for example, would require a composition containing at least 10% of the chelating blend for complete removal of copper. In the absence of the synergistic effect discovered above (Table 2), this would translate into yet higher, and rather unrealistic, composition containing over 30% of a single chelating agent. Needless to say, it is not even possible, to obtain compositions with such high concentrations of EDTA within practical pH ranges. This may explain why EDTA was found to be ineffective in prior art. The disodium salt of EDTA which is used in the greatest majority of prior art, usually in the form of acidic compositions around pH 5.0, has a solubility limit of about 10% at this pH. A comparison of the efficacy of copper removal by disodium EDTA at its saturation level, and a composition of the present invention is shown in Table 4. When such EDTA-saturated composition is applied to copper-contaminated hair, containing 4625 ppm copper, for a period of time as long as one hour at 55° C., it fails to clean the hair. In comparison, a composition containing an equivalent concentration of blended chelating agents consisting of 3.0% EDTA-$Na_4$, 5% HEEDTA-$Na_3$, and 2% EDG-$Na_2$, completely removes the copper, and it does so in one-third the time (Table 4).

TABLE 4

| Sample/Treatment | Residual copper (ppm) |
|---|---|
| Copper-contaminated hair (Cu-hair), untreated | 4625 |
| Cu-hair + 10% EDTA-$Na_2$, 1 hr at 55° C. | 955 |
| Cu-hair + 10% invention blend[(1)] (20 min. at 55° C.) | 14 |
| non-contaminated control, untreated | 16 |

[(1)]3.0% EDTA-$Na_4$, 5% HEEDTA-$Na_3$, 2% EDG-$Na_2$, and .5% xanthan gum

Example #5

Based on the above discoveries, blend compositions of specialized chelating agents have been designed by the present invention for the synergistic and complete removal of a wide range of minerals adsorbed to keratin fibers such as hair, wool and feathers. Exemplary compositions are shown in Table 5. The ingredients were added in the order shown while mixing. Sodium laureth sulfate is a surfactant, and citric acid is a pH adjuster. The usage of the term "laureth" in the above nomenclature is through acceptance by the Cosmetic, Toiletry and Fragrance Association (CTFA), the governing body of the cosmetic industry in the U.S., to denote that a certain fatty alcohol is ethoxylated. In this case, lauryl alcohol may be ethoxylated by adding up to four molecules of ethylene oxide. The general formula of sodium laureth sulfate is $CH_3(CH_2)_{10}CH_2(OCH_2CH_2)_nOSO_3Na$, where n in a preferred embodiment, averages between 1 and 4 inclusive. While sodium laureth sulfate is given as a specific example, other surfactants, whether nonionic, anionic, cationic, amphoteric, or blends thereof, may be used in conjunction with the above compositions. EDTA-$Na_4$ is tetrasodium salt of ethylenediaminetetraacetic acid; HEEDTA-$Na_3$, is the salt of hydroxyethyl-ethylenediaminetriacetic acid; EDG-$Na_2$ is the disodium salt of ethanoldiglycine; DTPA-$Na_5$ is the pentasodium salt of diethylenetriaminepentaacetic acid; NTA-$Na_3$ is the trisodium salt of nitrilotriacetic acid; STPP is sodium tripolyphosphate and HEDP is hydroxyethylidenediphosphonic acid.

These blends of chelating agents may be delivered in any of several vehicles. One vehicle of delivery could be as a dry powder containing one or more of the specified chelating species, in addition to a thickener or a gelling agent, and a pH adjuster in the form of citric acid to bring the pH into the specified range. The dry blend, which may be packaged in a tub, resealable bag, or packet, when mixed with water prior to use, will deliver a final concentration of active species in the range of 4 to 25%, and a pH range of 4 to 9. A second vehicle of delivery might be in the form of a shampoo, where surfactants, conditioners, fragrance, and other essential and cosmetic ingredients may be incorporated into a product. A third vehicle may be a creme, where emulsifiers and emulsifiable ingredients may be added. A fourth vehicle may be a mousse where surfactants and propellants may be included in an aqueous base in a pressurized container, together with the active species. It should be obvious that modifications to the vehicles are numerous, and the vehicle type should bear no impact on the present invention or the concept underlying it.

TABLE 5

| | Composition # | | | | |
|---|---|---|---|---|---|
| | 1 | 2 | 3 | 4 | 5 |
| Deionized water | 63.0 | 67.0 | 64.0 | 60.0 | 63.0 |
| Citric acid | 1.6 | 2.0 | 2.0 | 1.5 | — |
| EDTA-$Na_4$ | 3.4 | — | — | — | 2.5 |
| HEEDTA-$Na_3$ | 5.0 | 2.0 | 4.0 | 3.5 | 4.0 |
| EDG-$Na_2$ | 2.0 | — | 2.0 | 2.0 | — |
| DTPA-$Na_5$ | — | — | 3.0 | — | — |
| NTA-$Na_3$ | — | 4.0 | — | — | — |
| STPP | — | — | — | 8.0 | — |
| HEDP | — | — | — | — | 4.0 |
| NaOH (50%) | — | — | — | — | 1.5 |
| Sodium laureth sulfate | 25.0 | 25.0 | 25.0 | 25.0 | 25.0 |
| Composition pH | 7.5 | 7.3 | 7.0 | 6.5 | 7.2 |

Example #6

Composition #1 of the present invention (Table 5) was tested against commercial professional products which are marketed for salon use only as cleansing treatments for mineral-contaminated hair. The various products were applied to mineral-contaminated hair for 15 minutes (except where specified otherwise), at 55° C., and processed as described earlier. Residual copper was determined by atomic absorption spectroscopy. The values represent averages of two separate determinations. Table 6 shows the performance of these professional products, as well as Composition #1 of the present invention, in removing copper from copper-contaminated hair.

TABLE 6

| Sample & Treatment | Residual copper (ppm) |
|---|---|
| Copper-contaminated (Cu-hair), untreated | 7674 |
| Cu-hair + Johnson's Baby shampoo(1) | 4215 |
| Cu-hair + Malibu 2000's crystal gel treatment(2) | 3835 |
| Cu-hair + Malibu 2000's, applied for 45 minutes at 55° C. | 3364 |
| Cu-hair + Clairol Professional's Metalex(3) | 3022 |
| Cu-hair + Nexxus' Aloe Rid clarifying treatment(4) | 4050 |
| Cu-hair + Joico's Phine chelating treatment(5) | 3310 |
| Cu-hair + Mastey's Le Remouver hair clarifier(6) | 3635 |
| Cu-hair + KMS's pHinish special care(7) | 2743 |
| Cu-hair + Action 3-step system for chlorine(8) | 3190 |
| Cu-hair + Abba's molasses purifying treatment(9) | 2691 |
| Cu-hair + composition #1 of present invention(10) | 91 |
| non-contaminated hair, control | 35 |

(1)Johnson & Johnson, Skillman, NJ
(2)Malibu 2000, Malibu, CA
(3)Clairol, Inc., Stamford, CT
(4)Nexxus Prod. Co., Santa Barbara, CA
(5)Joico Lab., Inc., Los Angeles, CA
(6)Mastey De Paris Inc., Valencia, CA
(7)KMS Research Inc., Redding, CA
(8)Action Environmental Prod., Agoura Hills, CA
(9)Abba Products, Inc., Irvine, CA
(10)Composition #1, Table 5

Example #7

Table 7 presents comparative data for the removal of iron from iron-contaminated hair by the various professional products and by composition #1 of the present invention. Experimental conditions and products are as specified in Table 6.

TABLE 7

| Sample & Treatment | Residual iron (ppm) |
|---|---|
| Iron-contaminated (Fe-hair), untreated | 3671 |
| Fe-hair + Johnson's Baby shampoo | 1690 |
| Fe-hair + Malibu 2000's crystal gel treatment | 237 |
| Fe-hair + Clairol Professional's Metalex | 1283 |
| Fe-hair + Nexxus' Aloe Rid clarifying treatment | 2237 |
| Fe-hair + Joico's Phine chelating treatment | 1644 |
| Fe-hair + Mastey's Le Remouver hair clarifier | 1854 |
| Fe-hair + KMS's pHinish special care | 2026 |
| Fe-hair + composition #1 of present invention | 137 |
| non-contaminated hair, control | 220 |

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A process for the removal of at least one exogenous metal ion selected from the group consisting of copper, iron, lead, zinc, aluminum, cadmium, calcium and magnesium which have become attached to human hair or animal keratin fiber with an air-stable composition comprising the sequential steps of:

(a) contacting the composition which contains at least one chelating agent to the human hair or animal keratin fiber at a pH of between 4 and 9 and at a concentration of between 4% to 25% by weight inclusive, the chelating agent selected from the group consisting of amino acid chelating agents, polyphosphate chelating agents and phosphonate chelating agents, and wherein when the chelating agent is (A) an amino acid chelating agent, the chelating agent is of formula (I)

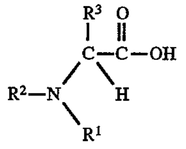

(I)

where $R^1$ is $CH_2$—Y;

Y is selected from the group consisting of $CO_2M$, $CH_2OH$, and H;

M is selected from the group consisting of H, Na, and K; and $R^2$ is represented by formula (II);

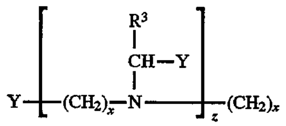

(II)

where

Y is selected from the group consisting of $CO_2M$, $CH_2OH$, and H;

M is selected from the group consisting of H, Na, and K;

x is an integer subscript ranging from 0 to 4;

z is an integer subscript ranging from 0 to 3; and $R^3$ is selected from the group consisting of H and a phenyl moiety represented by formula (III)

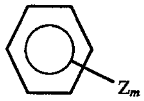

(III)

where

Z is an hydroxyl group; and m is a subscript ranging from 0 to 3, (B) a polyphosphate chelating agent, the chelating agent is selected from the group consisting of the linear polyphosphates of formula (IV)

$$[P_nO_{3n+1}]^{(n+2)-}M_{n+2}^+ \quad (IV)$$

where

M is selected from the group consisting of H, Na, and K and cyclic polyphosphates of formula (V)

$$[P_nO_{3n}]^{n-}M_n^+ \quad (V)$$

where

M is selected from the group consisting of H, Na, and K and (C) a phosphonate chelating agent, the chelating agent is selected from the group consisting of formula (VI)

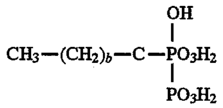

(VI)

and formula (VII)

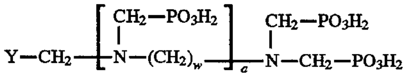

(VII)

where b is an integer subscript from 0 to 6;

a is an integer from 0 to 3;

w is an integer subscript from 2 to 8;

Y is selected from the group consisting of $CO_2M$, $CH_2OH$, and H; and

M is selected from the group consisting of H, Na, and K; and (b) contacting the composition which contains at least one chelating agent with the human hair or animal keratin fiber for at least two minutes allowing the chelating agent to complex with the exogenous metal ions; and (c) rinsing the composition which contains at least one chelating agent from the human hair or animal keratin fiber.

2. The process of claim 1 wherein the pH is adjusted to a range of between 5 to 8.

3. The process of claim 1 wherein the chelating agent is added at a concentration of 5% by weight to 20% by weight.

4. The process of claim 3 wherein heat is applied after step (a) to the human hair or animal keratin fiber.

5. The process of claim 1 wherein the chelating agent is a sodium salt.

6. The process of claim 1 wherein the chelating agent is a blend of chelating agents.

7. A process for the removal of at least one exogenous metal ion selected from the group consisting of copper, iron, lead, zinc, aluminum, cadmium, calcium and magnesium which have become attached to human hair or animal keratin fiber comprising the sequential steps of:

(a) contacting a composition which contains at least one chelating agent to the human hair or animal keratin fiber at a pH of between 4 and 9 and at a concentration of between 4% to 25% by weight inclusive, the chelating agent selected from the group consisting of amino acid chelating agents, polyphosphate chelating agents and phosphonate chelating agents, and wherein when the chelating agent is (A) an amino acid chelating agent, the chelating agent is a blend of at least two different amino acid chelating agents of formula (I)

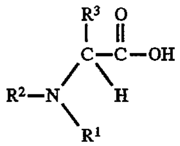

(I)

where $R^1$ is $CH_2$—Y;

Y is selected from the group consisting of $CO_2M$, $CH_2OH$, and H;

M is selected from the group consisting of H, Na, and K; and $R^2$ is represented by formula (II);

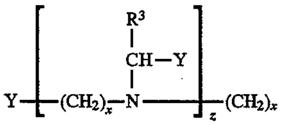

(II)

where

Y is selected from the group consisting of $CO_2M$, $CH_2OH$, and H;

M is selected from the group consisting of H, Na, and K;

x is an integer subscript ranging from 0 to 4;

z is an integer subscript ranging from 0 to 3; and $R^3$ is selected from the group consisting of H and a phenyl moiety represented by formula (III)

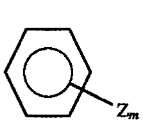

(III)

where

Z is an hydroxyl group; and m is a subscript ranging from 0 to 3, (B) a polyphosphate chelating agent, the chelating agent is selected from the group consisting of the linear polyphosphates of formula (IV)

$[P_nO_{3n+1}]^{(n+2)-}M_{n+2}^+$ (IV)

where

M is selected from the group consisting of H, Na, and K and cyclic polyphosphates of formula (V)

$[P_nO_{3n}]^{n-}M_n^+$ (V)

where

M is selected from the group consisting of H, Na, and K; and (C) a phosphonate chelating agent, the chelating agent is selected from the group consisting of formula (VI)

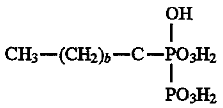

(VI)

and formula (VII)

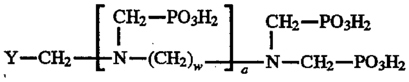

(VII)

where b is an integer subscript from 0 to 6;

a is an integer from 0 to 3;

w is an integer subscript from 2 to 8;

Y is selected from the group consisting of $CO_2M$, $CH_2OH$, and H; and

M is selected from the group consisting of H, Na, and K;

(b) contacting the composition which contains at least one chelating agent with the human hair or animal keratin fiber for for at least two minutes, allowing the chelating agent to complex with the exogenous metal ions; and (c) rinsing the composition which contains at least one chelating agent from the human hair or animal keratin fiber.

8. The process of claim 7 wherein the pH is adjusted to a range of between 5 to 8.

9. The process of claim 7 wherein the chelating agent is added at a concentration of 4% by weight to 25% by weight.

10. The process of claim 9 wherein the chelating agent is added at a concentration of 5% by weight to 20% by weight.

11. The process of claim 7 wherein heat is applied after step (a) to the human hair or animal keratin fiber.

12. The process of claim 7 wherein the chelating agent is a sodium salt.

13. The process of claim 7 wherein the chelating agent is at least two or more chelating agents.

14. A process for the removal of at least one exogenous metal ion selected from the group consisting of copper, iron, lead, zinc, aluminum, cadmium, calcium and magnesium which have become attached to human hair or animal keratin fiber with an air-stable composition consisting essentially of the sequential steps of:

(a) contacting the composition which contains at least one chelating agent to the human hair or animal keratin fiber at a pH of between 4 and 9 and at a concentration of between 4% and 25 % by weight inclusive, the chelating agent selected from the group consisting of amino acid chelating agents, polyphosphate chelating agents and phosphonate chelating agents, and wherein when the chelating agent is (A) an amino acid chelating agent, the chelating agent is of formula (I)

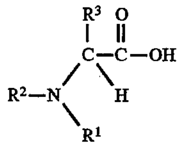

(I)

where $R^1$ is $CH_2$—Y;

Y is selected from the group consisting of $CO_2M$, $CH_2OH$, and H;

M is selected from the group consisting of H, Na, and K; and $R^2$ is represented by formula (II);

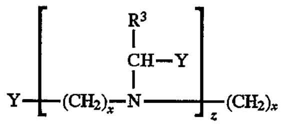

(II)

where

Y is selected from the group consisting of $CO_2M$, $CH_2OH$, and H;

M is selected from the group consisting of H, Na, and K;

x is an integer subscript ranging from 0 to 4;

z is an integer subscript ranging from 0 to 3; and $R^3$ is selected from the group consisting of H and a phenyl moiety represented by formula (III)

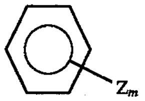

(III)

where

Z is an hydroxyl group; and m is a subscript ranging from 0 to 3, (B) a polyphosphate chelating agent, the chelating agent is selected from the group consisting of the linear polyphosphates of formula (IV)

$$[P_nO_{3n+1}]^{(n+2)-}M_{n+2}^{+} \qquad \text{(IV)}$$

where

M is selected from the group consisting of H, Na, and K and cyclic polyphosphates of formula (V)

$$[P_nO_{3n}]^{n-}M_n^{+} \qquad \text{(V)}$$

where

M is selected from the group consisting of H, Na, and K and (C) a phosphonate chelating agent, the chelating agent is selected from the group consisting of formula (VI)

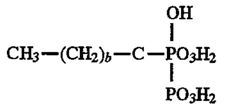

(VI)

and formula (VII)

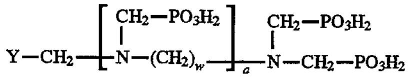

(VII)

b is an integer subscript from 0 to 6;

a is an integer from 0 to 3;

w is an integer subscript from 2 to 8;

Y is selected from the group consisting of $CO_2M$, $CH_2OH$, and H; and

M is selected from the group consisting of H, Na, and K; and (b) contacting the chelating agent with the human hair or keratin fiber for at least two minutes allowing the chelating agent to complex with the exogenous metal ions; and (c) rinsing the chelating agent from the human hair or keratin fiber.

15. The process of claim 14 wherein the pH is adjusted to a range of between 5 to 8.

16. The process of claim 14 wherein the chelating agent is added at a concentration of 4% by weight to 25% by weight.

17. The process of claim 16 wherein the chelating agent is added at a concentration of 5% by weight to 20% by weight.

18. The process of claim 14 wherein heat is applied after step (a) to the human hair or animal keratin fiber.

19. The process of claim 14 wherein the chelating agent is a sodium salt.

20. The process of claim 14 wherein the chelating agent is a blend of chelating agents.

* * * * *